Figure 2:
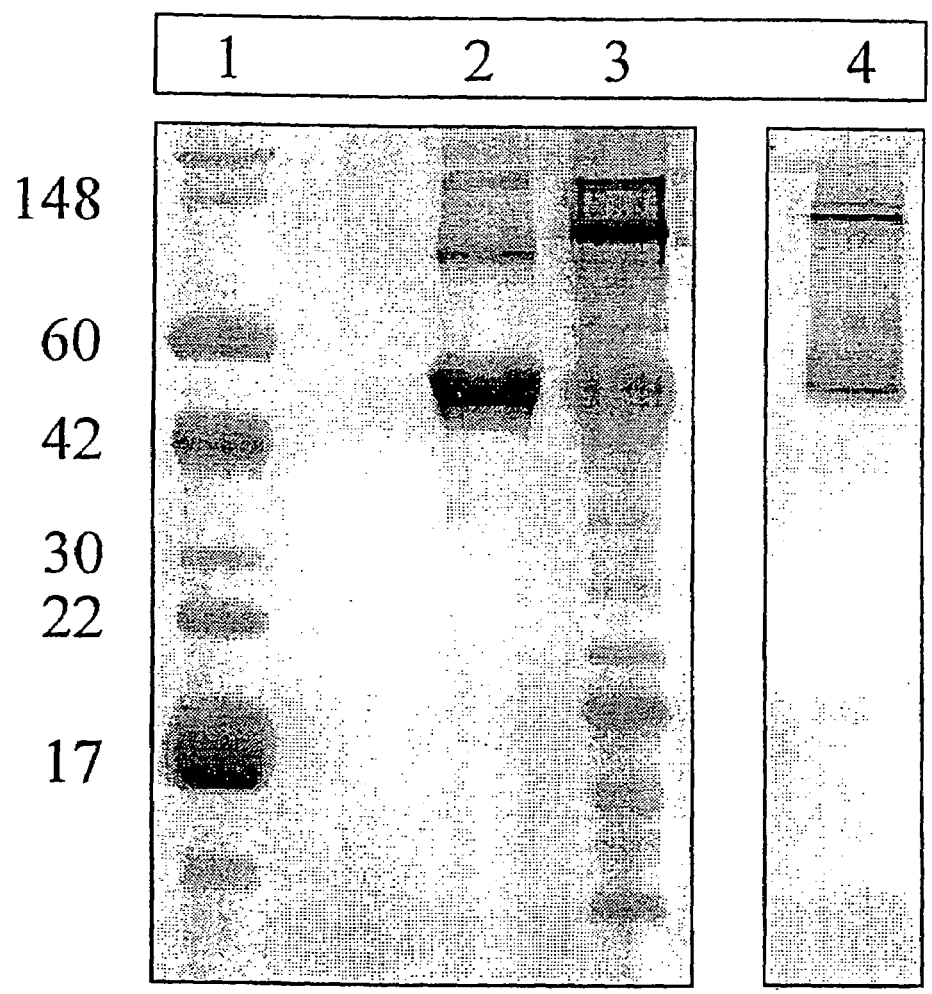

US007009090B1

(12) United States Patent
Dall

(10) Patent No.: US 7,009,090 B1
(45) Date of Patent: Mar. 7, 2006

(54) PLANTS AND FEED BAITS FOR CONTROLLING DAMAGE FROM FEEDING INSECTS

(75) Inventor: David James Dall, Downer (AU)

(73) Assignee: Commonwealth Scientific and Industrial Research Organisation, Australian Capital Territory (AU)

( * ) Notice: Subject to any disclaimer, the term of this patent is extended or adjusted under 35 U.S.C. 154(b) by 0 days.

(21) Appl. No.: 09/936,216

(22) PCT Filed: Mar. 10, 2000

(86) PCT No.: PCT/AU00/00181

§ 371 (c)(1), (2), (4) Date: Jan. 23, 2002

(87) PCT Pub. No.: WO00/53000

PCT Pub. Date: Sep. 14, 2000

(30) Foreign Application Priority Data

Mar. 10, 1999 (AU) ..................................... PP9113

(51) Int. Cl.
*A01H 5/00* (2006.01)
*C12N 15/82* (2006.01)
*C12N 15/90* (2006.01)

(52) U.S. Cl. ...................................... 800/302; 435/468
(58) Field of Classification Search ................ 435/418, 435/419, 468; 800/278, 279, 302
See application file for complete search history.

(56) References Cited

U.S. PATENT DOCUMENTS 5,877,194 A * 3/1999 Colliot et al. ............... 514/383

FOREIGN PATENT DOCUMENTS

| | | |
|---|---|---|
| EP | 0 596 508 | 5/1994 |
| WO | WO 93/25666 | 12/1993 |
| WO | WO 97/12906 | 4/1997 |
| WO | WO 00/36128 A | 6/2000 |

OTHER PUBLICATIONS

Adang et al., Plant Mol. Biol., 1993, vol. 21, pp. 1131-1145.*
Mitsuhashi, et al., The Spindles Of An Entomopoxvirus of Coleoptera (*Anomala Cuprea*) Strongly Enhance the Inefectivity of a Nucleopolyhedrovirus in Lepidoptera (Bombyx Mori), Journal Of Invertebrate Pathology, vol. 71, 1998, P.P. 186-188.
Tomita, et al. "Serological Relationship Between Inclusion Body Proteins and a Virus Enhancing Factor Of An Entomopxvirus," Appl. Entomol Zool., vol. 33(2), 1998, P.P. 277-280.
Xu and Hukuhara, "Enhanced Infection Of a Nuclear Polyhedrosis Virus in Larvae Of The Armyworm, Pseudaletia Separata, By a factor In The Spheroiuds Of An Entomopoxvirus," Journal of Invertebrae Pathology, vol. 60, 1992, PP. 259-264.
Dall, et al. " A Gene Encoding A Highly Expressed Spindle Body Protein Of Heliothis Armigera Entomopoxvirus," Journal of General Virology, vol. 74, 1993, PP. 1811-1818.
Xu and Hukuhara, "Biochemical Properties Of An Enhancing Factor Of An Entomopoxvirus," Journal Of Invertebrae Pathology, vol. 63, 1994, PP. 14-18.
Chemical Abstracts Online Accession No. 125:295128, Kagaku to Seibutsu, vol. 34(9), 1996, Hayakawa and Takahiko, " Glycoprotein Promoting Infection By Insect Virus," PP. 562-564.
Hayakawa, et al., "Cloning and Sequencing Of the Gene For An Enhancing Factor From Pseudaletia Separata Entomopoxvirus," Gene, vol. 177, 1996, PP. 269-270.
Gauthier, et al., The Melolontha Melolontha Entomopoxvirus (MmEPV) Fusolin Is Related To The Fusolins of Lepidopteran EPVs and to the 37K Baculovirus Glycoprotein, Virology, vol. 208, 1995, PP. 427-436.

Hukuhara Tosihiko et al: "Increased baculovirus susceptibility of armyworm larvae feeding on transgenic rice plants expressing an entomopoxvirus gene." Nature Biotechnology, vol. 17, No. 11, Nov. 1999 pp. 1122-1124, XP002231409.

Leborgne-Castle, Nathalie et al., "Overexpression of BIP in tobacco alleviates endoplasmic reticulum stress." Plant Cell, American Society of Plant Physiologists, vol. 11, No. 3, Mar. 1999 pp. 459-469, XP002137298, ISSN: 1040-4651.

Jean R. Adams et al., Histopathology of the Almond Moth, *Cadra cautella*, Infected with a Nuclear-Polyhedrosis Virus, Journal of Invertebrate Pathology 12, pp. 269-274, (1968).

Bernard Moss, Chapter 83, Poxviridae: The Viruses and Their Replication, Fields Virology, Third Edition, pp. 2637-2671.

R.H. Goodwin et al., Chapter 8, "ENTOMOPOXVIRINAE", Atlas of Invertebrate Viruses, 1991, pp. 259-285.

C.H. Ahrens et al., "The Sequence of the *Orgyia pseudotosugata* Multinucleocapsid Nuclear Polyhedrosis Virus Genome", Virology 229, pp. 381-399, (1997).

Basil M. Arif, Review Article, "Recent advances in the molecular biology of entomopoxviruses", Journal of General Virology, (1995), 76, pp. 1-13.

(Continued)

*Primary Examiner*—Ashwin Mehta
(74) *Attorney, Agent, or Firm*—McDermott Will & Emery LLP

(57) ABSTRACT

Plants are disclosed which are capable of expressing, in a tissue or tissues susceptible to damage by feeding insects, an exogenous protein(s) such as fusolin or a fusolin-like protein, to reduce damage to the plant by inhibiting feeding, growth and/or development of insects. Feed baits comprising spindle bodies, spindle-like bodies or constituent protein(s) thereof which inhibit feeding, growth and/or development of insects are also disclosed.

10 Claims, 7 Drawing Sheets

OTHER PUBLICATIONS

Martin D. Ayres et al., "The Complete DNA Sequence of *Autographa californica* Nuclear Polyhedrosis Virus", Virology 202, pp. 586-605, (1994).

John C. Cunningham, "An ultrastructural study of the development of a nuclear polyhedrosis virus of the eastern hemlock looper, *Lambdina fiscellaria fiscellaria*", Insect Pathology Research Institute, Department of Fisheries and Forestry, Jun. 22, 1970, pp. 69-72.

Carol A. Fernon et al., "Replication of *Heliothis armigera* Entomopoxvirus in Vitro", Journal of Invertebrate Pathology 66, pp. 216-223, (1995).

Sumiko Gomi et al., "Sequence analysis of the genome of *Bombyx mori* nucleopolyhedrovirus", Journal of General Virology, (1999), pp. 1323-1337.

Christian H. Gross et al., "A37-Kilodalton Glycoprotein from a Baculovirus of *Orgyia pseudotsugata* Is Localized to Cytoplasmic Inclusion Bodies", Journal of Virology, Jan. 1993, pp. 469-475.

Richard L. Hall et al., "Identification, Cloning and Sequencing of a ragment of *Amsacta moorei* Entomopoxvirus DNA Containing the Spheroiden Gene and Three Vaccinia Virus-Related Open Reading Frames", Journal of Virology, Dec. 1991, pp. 6516-6527.

John Kuzio et al., "Sequence and Analysis of the Genome of a Baculovirus Pathogenic for *Lymantria dispar*", Virology 253, pp. 17-34, (1999).

Joan Lai-Fook et al., "Spindle Bodies of *Heliothis armigera* Entomopoxvirus Develop in Structures Associated withHost Cell Endoplasmic Reticulum", Journal of Invertebrate Pathology 75, pp. 183-192, (2000).

Rebecca J. Osborne et al., "An entomopoxvirus homologue of the vaccinia virus D13L-encoded 'rifampicin resistance' protein", Journal of General Virology, (1996), 77, pp. 839-846.

C.G. Phanis et al., "Identification and expression of two baculovirus gp37 genes", Journal of General Virology, (1999), 80, pp.. 1823-1831.

W.A. Smirnoff, "Rhombohedral twisted crystalloids found in the cytoplasm of nuclear-polyhedrosis infected larvae of the ugly-nest caterpillar", Canadia Journal of Microbiology, vol. 16, 1970, pp. 906-907.

Algacone Sriskantha et al., "Mapping of the *Heliothis armigera* entomopoxvirus (HaEPV) genome, and analysis of genes encoding the HaEPV spheroidin and nucleoside triphosphate phosphohydrolase I proteins", Journal of General Virology, (1997), 78, pp. 3115-3123.

J. Jian Liu et al., Short Communication, "Identification, Molecular Cloning, and Transcription-Analysis of the *Choristoneura fumiferana* Nuclear Polyhedrosis Virus Spindle-like Protein Gene", Virology 223, pp. 396-400 (1996).

Tohru Hayakawa et al., "Sequence Analysis of the *Xestia c-nigrum* Granulovirus Genome", Virology 262, pp. 277-297, (1999).

Jean R. Adams et al., Chapter 6, "Baculoviridae Nuclear Polyhedrosis Viruses", Atlas of Invertebrate Viruses, pp. 87-204 (1991).

F.A. Murphy et al., "Virus Taxonomy, Classification and Nomenclature of Viruses", Sixth Report of the International Committee on Taxonomy of Viruses, pp. 79-113 (1995).

Alois M. Huger et al., "On Spindle-Shaped Cytoplasmic Inclusions Associated with a Nuclear Polyhedrosis of *Choristoneura murinana*", J. Invertebrate Pathology, Jul. 30, 1968, pp. 461-462.

\* cited by examiner

Figure 1

FIGURE 5

% infection vs dose (log spheroids/ mm² diet)

□ wtHaEPV 2D8 (fus[+])
◊ recHaEPV pp7T6 (fus[-])

PLANTS AND FEED BAITS FOR CONTROLLING DAMAGE FROM FEEDING INSECTS

FIELD OF THE INVENTION

The present invention relates to the problem of damage caused to plants (e.g. crop plants) from feeding insects such as lepidopterans and coleopterans. More particularly, the present invention relates to a plant capable of expressing, in a tissue or tissues susceptible to damage by feeding insects, an exogenous protein(s) which may reduce damage to the plant by inhibiting feeding, growth and/or development of insects.

BACKGROUND OF THE INVENTION

Entomopoxviruses (EPVs) are insect-specific members of the family Poxyiridae (Murphy et al., 1995) that collectively infect hosts such as caterpillars, beetles and locusts (Arif, 1995). Like other members of the poxvirus family (i.e., the chordopoxviruses; ChPVs), EPVs have large double-stranded DNA genomes, produce complex virions, and replicate in the cytoplasm of infected cells (Moss, 1996). While these and other molecular characteristics confirm their poxvirus affinities (Osborne et al., 1996), other notable traits differentiate EPVs from ChPVs, and ally them instead with unrelated groups of insect-infecting viruses. Foremost among these traits is production of the distinctive proteinaceous structures known as spheroids and spindle bodies.

Spheroids develop in the cytoplasm of EPV-infected cells at the site of viral morphogenesis, and when mature, occlude large numbers of infectious virions (Goodwin et al., 1991). They are the agent of horizontal transmission of EPVs, and while their major constituent matrix protein (spheroidin; Hall & Moyer, 1991) has no known homologue outside the taxon, the bodies themselves are assumed to protect virions from detrimental environmental factors such as desiccation and exposure to u.v. light. In this respect they are functionally analogous to the polyhedral bodies which occlude virions of members of the baculovirus family and the cytoplasmic polyhedrosis group of reoviruses.

Most EPVs also encode and produce a protein known as fusolin, which has been shown to be the major constituent of structures known as spindle bodies (SBs; Dall et al., 1993); these structures have been described from many, but not all, members of EPV genera A and B that infect caterpillars and beetle larvae (Goodwin et al., 1991). In the *Heliothis armigera* EPV (HaEPV)(Fernon et al., 1995), the fusolin protein has a calculated $M_r$ of 40132, and the mature form of the protein has an apparent size of 50K when analysed by SDS-PAGE (Dall et al., 1993). The protein has been found to accumulate in vesicular structures derived from cellular endoplasmic reticulum, where it eventually aggregates and crystallises into SBs (Lai-Fook and Dall, in press). Although other proteins are known to be co-located in SBs (e.g., the ER-specific chaperone protein, BiP; Lai-Fook and Dall, in press), analysis of purified SB preparations shows that fusolin, in its monomeric and multimeric forms (Dall et al., 1993), is by far the most abundant constituent.

Genes encoding homologues of the fusolin protein, in this context known variously as "gp37", "37K protein", "SLP" (spindle-like protein), etc., have also been described from a number of nuclear polyhedrosis (NPV) baculoviruses, including the *Autographa californica, Bombyx mori, Choristoneura fumiferana, Lymantria dispar, Orgyia pseudotsugata* NPVs and *Xestia c-nigrum* GV (AcMNPV, BmMNPV, CfMNPV, LdMNPV, OpMNPV and XcGV, respectively; Ayres et al., 1994; Gomi et al., 1999; Liu and Carstens, 1996; Kuzio et al., 1999; Ahrens et al., 1997; Hayakawa et al., 1999). In some of these (e.g., OpNPV; Gross et al., 1993), the protein has been observed within spindle-like bodies (SLBs) in the cytoplasm of infected cells. SLBs have also been observed in the cytoplasm of cells infected with other NPVs (e.g., from *Cadra cautella* NPV, Adams and Wilcox 1968; see also Adams and McClintock, 1991; Cunningham, 1971; Huger and Kreig, 1968; Smirnoff, 1970).

All members of the fusolin group of proteins, irrespective of their viral family of origin, are united by an absolute conservation of amino acid residues at a number of positions in their sequences, in particular in the N-terminal and central regions of the molecule. These conserved residues include HGX (standard one letter amino acid code, where X is an aromatic amino acid) and ARQ motifs near the N-terminal of the deduced protein sequence (Table 1), and e.g. a VRWQR (SEQ ID NO:1) sequence elsewhere within the deduced amino acid sequence (FIG. 1). This conservation of sequence elements, like that of the protein's intracellular location, as previously described, suggests that all members of the group also share a common role in the cycle of virus infection and replication, perhaps in influencing the relationship of the viruses with their hosts (Sriskantha et al., 1997). Nevertheless, the function(s) of members of this group of proteins, and the SB/SLB structures that they form, remain a topic of on-going investigation.

Studies by Xu and Hukuhara (1992, 1994) suggested that a factor associated with preparations of *Pseudaletia separata* EPV (PsEPV), and subsequently identified as fusolin (Hayakawa et al., 1996), was capable of enhancing the infectivity of a heterologous nuclear polyhedrosis virus (*P. unipunctata* NPV). Further studies have shown that a similar effect can be seen in transgenic rice plants in which this protein has been expressed (Hukuhara et al., 1999). Similarly, the SBs of the cupreous chafer (*Anomala cuprea*) have been shown to be capable of acting in the same manner (Mitsuhashi et al., 1998). The role(s) of fusolin protein in the context of homologous EPV systems has not, however, been previously subjected to detailed investigation.

Through experiments involving bioassays using SBs of *Heliothis* armigera EPV (HaEPV) and *Dermolepida albohirtum* EPV (DaEPV$_{SR}$), the present applicants have determined, unexpectedly, that consumption of spindle bodies alone can effect feeding, growth and development of insect larvae. Further, through experiments conducted using recombinant EPVs wherein the fusolin gene has been replaced with a β-galactosidase marker (i.e., to render the recombinant EPVs fusolin negative [fus$^{(-)}$]), the present applicants have also been able to provide evidence to show that it is the fusolin protein component of SBs that is responsible for these effects. Moreover, the latter experiments have indicated that fusolin enhances the infectivity of the homologous EPV virus. As a result, it has been realised that SBs, SLBs and constituent proteins of these structures may be advantageously used in strategies designed to reduce damage caused to plants by feeding insects.

SUMMARY OF THE INVENTION

In a first aspect, the present invention provides a plant transformed with at least one polynucleotide molecule comprising a nucleotide sequence(s) encoding one or more constituent protein(s) of spindle bodies or spindle-like bodies from an insect virus, operably linked to a suitable promoter sequence(s), wherein said transformed plant expresses said proteins) in, at least, plant tissue or tissues susceptible to damage by feeding insects.

In a second aspect, the present invention provides a feed bait composition comprising spindle bodies or spindle-like bodies from an insect virus, or one or more constituent protein(s) of said spindle bodies or spindle-like bodies, together with an agriculturally acceptable carrier.

DETAILED DISCLOSURE OF THE INVENTION

As mentioned above, the invention provides a plant capable of expressing one or more constituent SB/SIB protein(s) in tissues (e.g. leaf tissue or a product tissue such as fruit tissue) susceptible to damage by feeding insects. Thus, when feeding insects feed on a plant according to the invention, they will ingest, along with plant tissue, the expressed constituent SB/SLB protein(s). Since SBs/SLBs appear to inhibit feeding, growth and/or development of insects and, potentially, increase susceptibility to infection from insect pathogens (and thereby insect death), ingestion of one or more of the constituent SB/SLB protein(s) by feeding insects may reduce further damage to the plant. In addition, it is believed that inhibiting the feeding, growth and/or development of insects also increases the likelihood of insect death resulting from, for example, adverse environmental conditions, predators and chemical and other biological agents (e.g. pathogenic bacteria).

The plant according to the invention may be any plant of agricultural, arboricultural, horticultural or ornamental value that is susceptible to damage by feeding insects. Preferably, the plant is selected from plants of agricultural value such as cereals (e.g. wheat and barley), vegetable plants (e.g. tomato and potato) and fruit trees (e.g. citrus trees and apples). Other preferred plants include tobacco and cotton.

The polynucleotide molecule(s) comprising a nucleotide sequence encoding one or more constituent SB/SLB protein(s) operably linked to a suitable promoter sequence(s), may be any polynucleotide molecule(s) that may be stably segregated and retained in daughter cells. Preferably, the polynucleotide molecule(s) is stably integrated into a non-essential site within the plant genome (as may be achieved by the well known technique of homologous recombination).

Preferred constituent SB/SLB proteins are fusolins, fusolin-like proteins and the ER-specific chaperone BiP proteins and homologues thereof.

Preferred fusolin proteins include those from HaEPV, *Pseudaletia separata* EPV (PsEPV), *Choristoneura biennis* EPV (CbEPV) and *Dermolepida albohirtum* EPV (Stone River isolate; $DaEPV_{SR}$; Dall et al, unpublished). Most preferred is the fusolin from HaEPV such as is described in the present applicant's Australian Patent No. 668734, the disclosure of which is to be regarded as incorporated herein by reference.

The term "fusolin-like protein" refers to all insect virus proteins and functional fragments thereof which are capable of inhibiting feeding, growth and/or development in at least one insect species, and which preferably also increases susceptibility in at least one insect species to infection from at least one pathogen virus (e.g. a virus). As such, the term includes all proteins (and functional fragments thereof) from entomopoxviruses (EPVs), nuclear polyhedrosis (NPV) and granulosis (GV) baculoviruses, and all other insect viruses, that demonstrate ≧35% amino acid sequence identity (as calculated by the GCG Gap algorithm; Devereux et al., 1984) to the HaEPV fusolin protein and which include the following partial amino acid sequences: HGX (standard one letter amino acid code, where X is an aromatic residue), and ARQ motifs near the N-terminal, and VRWQR (SEQ ID NO:1) elsewhere. Preferred fusolin-like proteins include those from AcMNPV, BmMNPV, CfMNPV, LdMNPV, OpMNPV and XcGV.

Where the plant expresses more than one constituent SB/SLB protein, the plant may be transformed with a single polynucleotide molecule such that the proteins are expressed from single or multicistronic messenger RNA. Alternatively, the proteins might be expressed from two or more polynucleotide molecules co-transformed into the plant.

Where the plant expresses all of the constituent SB/SLB protein(s) of an insect virus, the protein(s) may be present in the plant tissues in the form of SB/SLB structures.

Suitable promoter sequence(s) for the expression of the nucleotide sequence(s) encoding the constituent SB/SLB protein(s), may be selected from any promoter sequence which is functional in plants. Preferred promoter sequences include those from plants, plant viruses and plant viroids. Particularly preferred promoter sequences include the cauliflower mosaic virus (CaMV 35S) promoter element, and promoter elements from the sub-clover stunt virus (SCSV).

Plants according to the present invention may also express an exogenous toxin or other exogenous agent that is deleterious to insects. For example, the plant may also express a *Bacillus thuringiensis* δ-toxin, an insect neurohormone, or an antisense RNA or ribozyme targeted against an essential cellular function. The heterologous toxin or deleterious agent may be encoded by a nucleotide sequence (operably linked to a suitable promoter sequence) borne on the polynucleotide molecule(s) encoding the one or more constituent SB/SLB protein(s) or may be borne on a further polynucleotide molecule which has been co-transformed into the plant.

Transformation of the plant with the polynucleotide molecule(s) may be achieved by any of the methods well known in the art including *Agrobacterium* transformation and electroporation.

As will be appreciated, the benefits achieved by expressing one or more constituent SB/SLB protein(s) in plants might also be achieved by producing feed baits comprising spindle bodies or spindle-like bodies from an insect virus, or one or more constituent protein(s) of said spindle bodies or spindle-like bodies. Thus, feed bait compositions according to the present invention comprise spindle bodies or spindle-like bodies from an insect virus, or one or more constituent protein(s) of said spindle bodies or spindle-like bodies, together with an agriculturally acceptable carrier.

The feed bait compositions may be in a liquid or gel form, but more preferably are in a solid form. The spindle bodies, spindle-like bodies or constituent SB/SLB protein(s) may comprise 0.05 to 15.0% (by weight) of the composition. In addition to the spindle bodies, spindle-like bodies or constituent SB/SLB protein(s) and the agriculturally acceptable carrier, the feed bait composition may further comprise a pheromone(s) or other chemical attractant to insects. For liquid formulations the agriculturally acceptable carrier may be selected from ingredients such as milled clays or edible carrier substances such as plant materials, molasses or raw sugar, and microorganisms such as yeasts or other fungi, algae or bacteria. For solid feed bait compositions, the agriculturally acceptable carrier may be selected from ground or fragmented plant material and other materials as described above processed to an appropriate form. The solid feed bait compositions may be provided as pellets and applied by casting over an area containing a plant for which protection against damage by feeding insects is desired. Liquid or gelled feed bait compositions may be applied to a plant by spraying.

The spindle bodies, spindle-like bodies or constituent SB/LB protein(s) included in the feed bait composition may be isolated from natural sources or, more conveniently, produced recombinantly in, for example, bacteria, yeast, insect or mammalian cell cultures.

Insects having ingested spindle bodies, spindle-like bodies or constituent SB/SLB protein(s) as the result of having fed on a plant or feed bait composition according to the present invention may, as mentioned above, be expected to cause reduced damage to plants either as a result of reduced feeding/growth and/or to have reduced life times as a result of an increased susceptibility to adverse environmental conditions or chemical and biological agents. Accordingly, the present invention further extends to methods where a plant in accordance with the first aspect or a plant to which a feed bait composition in accordance with the second aspect has been applied, is treated with an insecticidal chemical and/or biological agent, and especially one whose activity has been shown to be higher against smaller, as compared to larger, insect larvae. Suitable chemical agents include organophosphate compounds and suitable biological agents include pathogenic bacteria and insect viruses (especially Bacillus thuringiensis [Bt] and nuclear polyhedrosis baculoviruses). These agents may be applied by any of the methods well known in the art and, most conveniently, by spraying. Preferably, the chemical or biological agent is applied in the form of a composition comprising an agriculturally acceptable carrier. Where used with a feed bait composition, it is to be understood that the feed bait composition might also be applied to the plant before, after or concurrently with the chemical and/or biological agent.

The terms "comprise", "comprises" and "comprising" as used throughout the specification are intended to refer to the inclusion of a stated component, feature or step or group of components, features or steps with or without the inclusion of a further component, feature or step or group of components, features or steps.

The invention is hereinafter described with reference to the accompanying figures and the following, non-limiting examples.

BRIEF DESCRIPTION OF THE ACCOMPANYING FIGURES

FIG. 1: Provides a comparison of a partial amino acid sequence of the fusolin protein of *Dermolepida albohirtum* entompoxvirus (Stone River isolate; DaEPV$_{SR}$) with corresponding regions of the same protein from other selected entompoxviruses and baculoviruses. Boxed text shows DaEPV$_{SR}$ fusolin sequence as determined by N-terminal amino acid analysis (bold) or conceptual translation of coding nucleotide sequence. Asterisks above the boxed DaEPV$_{SR}$ sequence show residues that differ from others of beetle-derived EPVs (MmEPV and AcEPV); those below the alignment show residues conserved across conceptual proteins from EPVs, NPVs and Gvs. (MmEPV: *Melolontha melolontlia* EPV; AcEPV: *Anomala cuprea* EPV; CbEPV: *Choristoneura biennnis* EPV; HaEPV: *Heliothis armigera* EPV; BmNPV: *Bombyx mori* nuclear polyhedrosis virus [NPV]; CfNPV: *Choristoneura fumiferanae* NPV; XcGV: *Xestia c-nigrum* granulosis virus).

FIG. 2: Provides a reproduction of a Coomassie blue stained SDS-PAGE gel of fractionated spindle bodies from HaEPV and DaEPV$_{SR}$.

Figure 3:
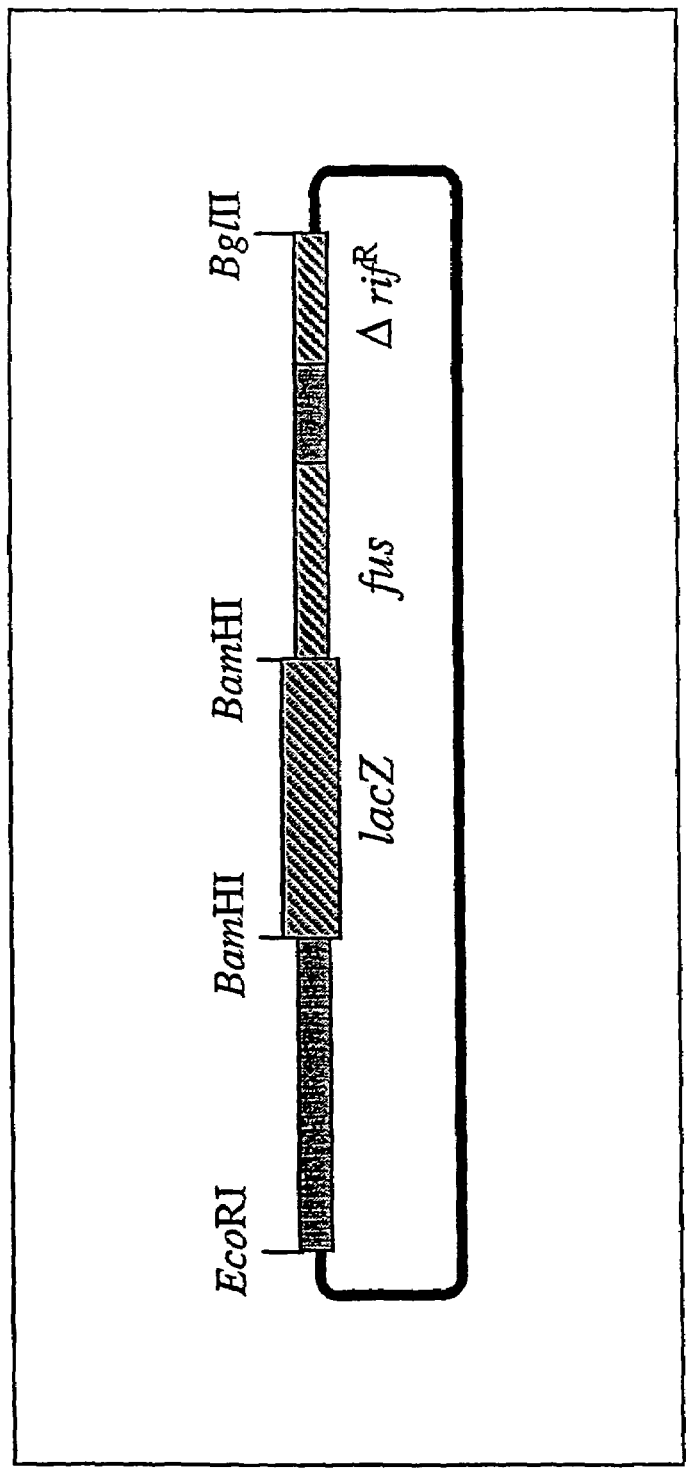

FIG. 3: Provides a map for the transfer vector pEPAS3.

Figure 4:
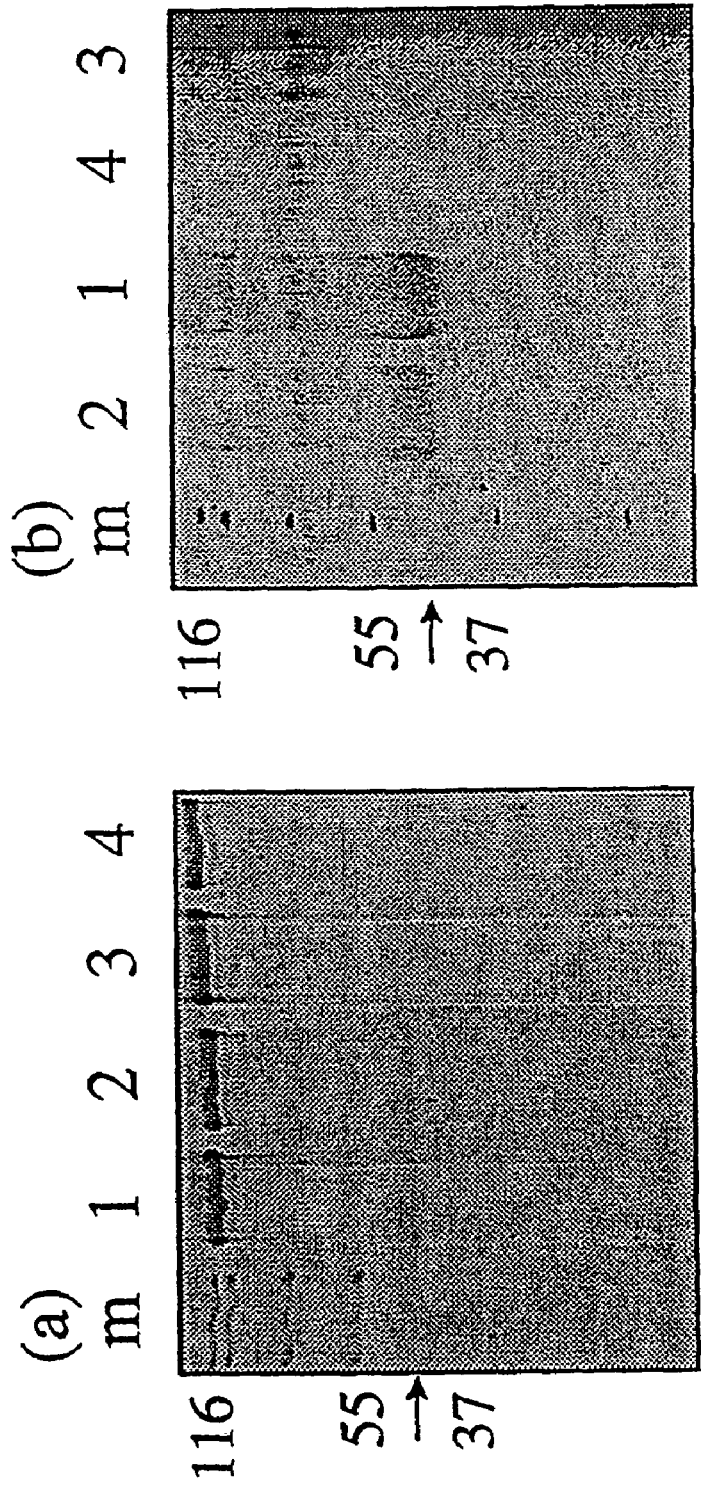

FIG. 4: Shows protein constituents of wild-type and recombinant [fus$^{(-)}$] isolates of HaEPV, visualised (a) by staining with Coomassie Blue, or (b) by Western blotting with antiserum to HaEPV fusolin. Arrows indicate positions of fusolin protein.

FIG. 5: Infectivity of wild-type and recombinant [fus$^{(-)}$] isolates of HaEPV for 48 hr old *Helicoverpa armigera* larvae.

Figure 6:
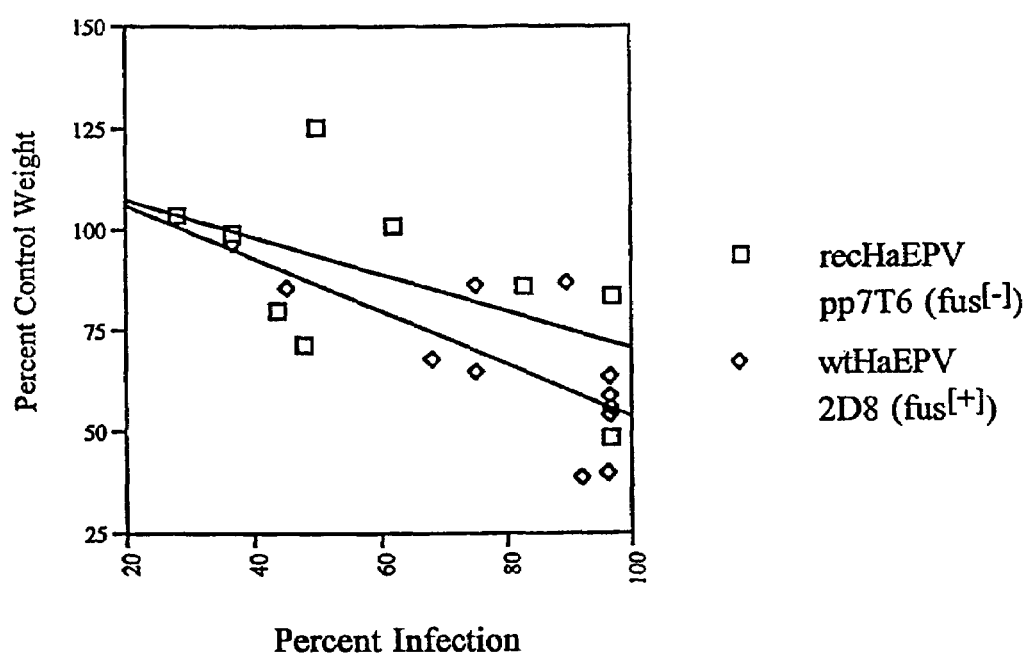

FIG. 6: Shows weight gain profiles of 48 hr old *Helicoverpa armigera* larvae after 7 days feeding on diet contaminated with wild-type and recombinant [fus$^{(-)}$] isolates of HaEPV.

Figure 7:
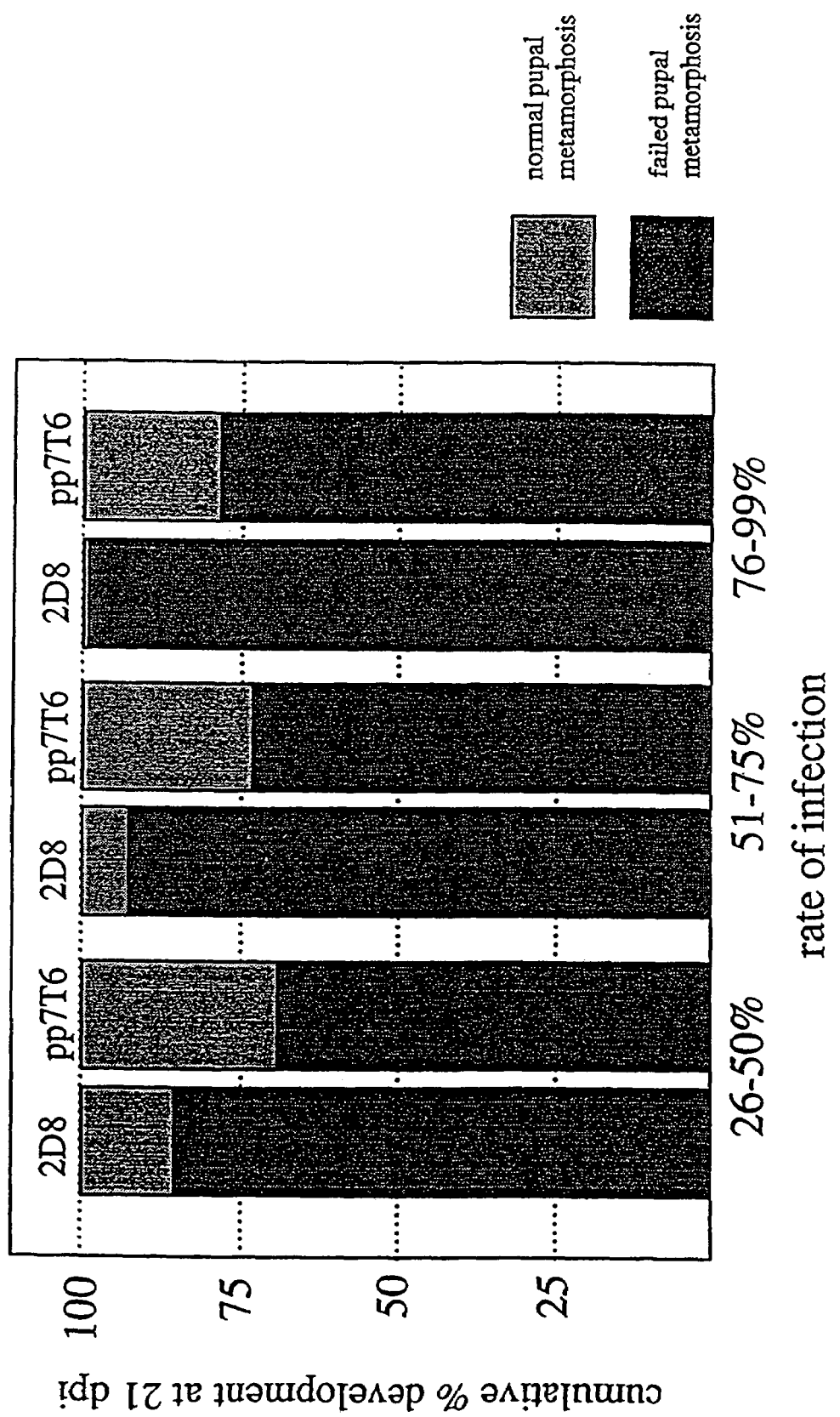

FIG. 7: Shows the developmental fate of 48 hr old *Helicoverpa armigera* larvae after 21 days feeding on diet contaminated with wild-type and recombinant [fus$^{(-)}$] isolates of HaEPV.

EXAMPLE 1

Separation Techniques for Purification/Isolation of HaEPV and DaEPV$_{SR}$ Viruses and Spindle Bodies Preparations of spheroids and spindle bodies (SBs) of *Heliothis armigera* entomopoxvirus (HaEPV) and *Dermolepida albohirtum* entomopoxvirus (DaEPV$_{SR}$) were made from macerated cadavers of larvae of *Spodoptera litura* (Lep: Noctuidae) and *Dermolepida albohirtum* (Col: Melolonthinae), respectively, using a process of repeated differential centrifugation. These preparations were layered onto a 36% (w/w) solution of CsCl and spun overnight at 27000 rpm in a Beckman SW41 rotor. Fractions containing high numbers of spindle bodies were collected and pooled, and the process was repeated until a sufficient degree of purity was obtained. Purified preparations of SBs were washed three times in phosphate-buffered saline (PBS), then stored at 5° C. in the same solution until use.

Preparations were analysed by light microscopy (LM) and by examination of protein composition by SDS-PAGE, the latter using techniques previously described (Dall et al., 1993). These protocols showed that a very high level of purity could be achieved for HaEPV (FIG. 2, lane 2), and that a satisfactory degree of purity could be obtained for DaEPV$_{SR}$ (FIG. 2, lane 4).

Partial Characterisation of DaEPV$_{SR}$ Fusolin

Protein constituents of preparations of DaEPV$_{SR}$ were separated by SDS-PAGE and immobilised by western blotting onto PVDF membrane (Dall et al., 1993). A band corresponding to a protein of about 50K $M_r$, and thus representing the putative DaEPV$_{SR}$ fusolin protein, was isolated, and the N-terminal amino acid sequence of the immobilised protein was obtained by use of an Applied Biosystems Procise Sequencer.

The resultant amino acid sequence (HGYITFPIARQRR (SEQ ID NO: 2); standard one letter code) was compared with others in GenBank using the NCBI Blast algorithm (Altschul et al., 1990). This and other analyses (using the GCG Gap algorithm) showed that this sequence corresponded to those known from fusolin/gp37 proteins from baculoviruses (nuclear polyhedrosis and granulosis viruses; NPVs and GVs, respectively), and other EPVs, and that it most closely matched forms of the protein previously identified from EPV isolates from coleopteran hosts (viz., *Melolontha melolontha* EPV [GenBank accession X77616], with which it was identical, and *Anomala cuprea* EPV [AB0007801]; Table 1).

TABLE 1

Alignment of the N-terminal amino acid sequence of DaEPV$_{SR}$ fusolin with other selected sequences.

| Virus | Sequence | Sequence Listing No. | GenBank Accession |
|---|---|---|---|
| Dermolepida albohirtum EPV (Stone River isolate) | HGYITFPIARQRR | SEQ ID NO: 2 | |
| Melolontha melolontha EPV | HGYITFPIARQRR | SEQ ID NO: 2 | (X77616) |
| Anomala cuprea EPV | HGYVTFPIARQRR | SEQ ID NO: 3 | (AB000780) |
| Choristoneura biennis EPV | HGYMTFPIARQRR | SEQ ID NO: 4 | (M34140) |
| Heliothis armigera EPV | HGYMTFPIARQRR | SEQ ID NO: 4 | (L08077) |
| Pseudaletia separata EPV | HGYMTFPIARQRR | SEQ ID NO: 4 | (BAA09138) |
| Bombyx mori NPV | HGYLSLPTARQYK | SEQ ID NO: 5 | (U55071) |
| Choristoneura fumiferana NPV | HGYLSVPVARQYK | SEQ ID NO: 6 | (U26734) |
| Mamestra brassica NPV | HGYLSYPVARQYK | SEQ ID NO: 7 | (AF108960) |
| Xestia c-nigrum GV | HGFMLYPLARQYR | SEQ ID NO: 8 | (AF162221) |
| conserved residues | **....*.***.. | | |

Genomic DNA of DaEPV$_{SR}$ was prepared by dissolution of purified preparations of spheroids/SBs in a high pH, carbonate buffer containing 40 mM thioglycollic acid. After the dissolution of spheroids/SBs was essentially complete (as assessed by LM examination), the solution was neutralised by addition of 10 mM Tris buffer, pH8.0, digested with protease K for 3 hr, boiled for 10 minutes then centrifuged at 15K g for 10 minutes to remove residual debris. The viral genomic DNA was collected with the supernatant and stored at −20° C. Viral genomic DNA was used as template in polymerase chain reaction (PCR) protocols with custom oligonucleotide primers (oligos).

A segment of the DaEPV$_{SR}$ fusolin-encoding gene was amplified by use of custom oligos NFUS1 and EPSP6.

Oligo NFUS1 was designed by reverse translation of the DaEPV$_{SR}$ N-terminal amino acid sequence described above, and comprised the sequence:

(NFUS1) 5'-cay ggw tat atr can ttt cct ata gc-3' (SEQ ID NO:9), where n represents any nucleotide, r=a or g, w=a or t, and y=c or t.

Oligo EPSP6 was designed to bind to a region known to be highly conserved in other forms of the gene, located some 700 nucleotides downstream of the translation initiation codon, and comprised the sequence:

(EPSP6) 5'-aca rtt rta raa wcc ttc wcc yac-3' (SEQ ID NO: 10), where n represents any nucleotide, r=a or g, w=a or t, and y=c or t.

PCR amplifications using oligo pair NFUS1 and EPSP6 and DaEPV$_{SR}$ DNA gave rise to a product of approximately 700 bp, as assessed by agarose gel electrophoresis. This product was cloned into plasmid pGem-TEasy (Promega), in order to allow characterisation of its constituent nucleotide sequence. The plasmid was replicated in Escherichia coli strain DH10β, and purified with a commercial reagent/protocol (Wizard Prep; Promega).

Analysis of the amplified nucleotide sequence used universal forward and reverse oligo nucleotides, with Elmer Perkin "Big Dye" reaction mix and PCR cycle sequence methodology as recommended by that supplier. Products of the sequencing reaction were analysed on an ABA377 DNA sequencer. The DNA sequence obtained was analysed using the GCG Map and Translate algorithms (Devereux et al., 1984); related sequences were obtained from GenBank using the NCBI Blast algorithm.

Comparative sequence analyses used GCG Gap and PileUp algorithms (Devereux et al., 1984). As shown in Table 1, the available DaEPV$_{SR}$ fusolin amino acid sequence shows closest relationships to analogous regions (as construed by alignment from the N-termini of the mature forms) of fusolin proteins from EPVs of coleopteran hosts (MmEPV and AcEPV), but also shows significant levels of sequence identity to other fusolin and gp37 proteins from EPVs and baculoviruses, respectively, from lepidopteran hosts.

Alignment of conceptual amino acid sequences (FIG. 1) shows that DaEPV$_{SR}$ fusolin has a unique sequence (as indicated by asterisks above the line, which show positions that differ with respect to other sequences of coleopteran EPV origin), but also that it retains the same groupings of conserved residues found in related proteins from other EPVs and baculoviruses from coleopteran and lepidopteran origins (asterisks below the alignment). As shown in Table 2, percentage identities between selected fusolin sequences range from 38.0 to 89.7% for HaEPV (complete molecule) and 45.2 to 81.8% for DaEPV$_{SR}$ (corresponding regions).

TABLE 2

Relationships of deduced HaEPV and DaEPV$_{SR}$ fusolin proteins with homologues from other entomopox- and baculovirus sources.

| | | | % identity | % similarity |
|---|---|---|---|---|
| [a]HaEPV | / PsEPV | | 89.7 | 92.9 |
| | / CbEPV | | 62.9 | 72.6 |
| | / AcEPV | | 55.5 | 71.3 |
| | / MmEPV | | 52.3 | 67.6 |
| | / MbNPV | | 46.3 | 61.2 |
| | / BmNPV | | 42.8 | 61.6 |
| | / XcGV | | 41.7 | 63.6 |
| | / CfNPV | | 38.0 | 58.8 |
| [b]DaEPV$_{SR}$ | / MmEPV | (19–238) | 81.8 | 87.3 |
| | / AcEPV | (17–236) | 72.7 | 81.4 |
| | / CbEPV | (21–241) | 60.5 | 75.0 |
| | / HaEPV | (21–240) | 63.6 | 78.2 |
| | / BmNPV | (20–236) | 47.7 | 62.0 |
| | / CfNPV | (20–236) | 45.2 | 61.8 |
| | / XcGV | (19–225) | 47.0 | 66.8 |

Identities and GenBank accession numbers of viruses/sequences shown in Table 2 are as presented in Table 1.
[a]Comparison of HaEPV fusolin with other viral homologues employs deduced full length protein sequences, using the GCG Gap algorithm at default gap weight and penalty settings.
[b]Comparison of DaEPV$_{SR}$ fusolin with other homologues employs the deduced partial DaEPV sequence as presented in FIG. 1, and the corresponding regions of other fusolin homologues, also as shown in FIG. 1. Those regions of the latter proteins are identified in Table 2 (in brackets) by their amino acid residue numbers in their respective full length sequences. Comparisons used the GCG Gap algorithm as described above.

Bioassay of Spindle Body Constituents Against Caterpillars

Purified SBs of HaEPV and DaEPV$_{SR}$ were incorporated into artificial insect diet by addition and mixing when the preparation was at a temperature just above solidification point. Diet was then allowed to solidify, and was administered to neonate larvae of *Helicoverpa armigera* and *Spodoptera litura*. Larvae were individually housed, and were reared in darkness at a constant temperature of 28° C. Larval weights and developmental status were assessed periodically; resultant pupae were stored at 5° C. prior to examination (see below).

Care was taken to exclude any contribution of contaminant virus infection to outcomes of experiments. In the case of experiments using HaEPV, weights and development times of individual larvae were included in analyses only when (1) the individual larva successfully pupated and showed a normal pupal morphology, and (2) the resultant pupa was judged not to be infected by virus, as assessed by examination of tissue by light microscopy. Thus, in these experiments every individual pupa was examined before inclusion of associated data into analyses. In the case of experiments using DaEPV$_{SR}$, previous work has shown that neither caterpillar species used in bioassays here is susceptible to infection with this beetle-derived pathogen. Nevertheless, as above, data were only included in analyses in cases where individual larvae successfully pupated and showed a normal pupal morphology; in these experiments however, only pupae from larvae exposed to the highest dosage of DaEPV$_{SR}$ spindle bodies in any given experiment were assessed for the presence of virus. This methodology was designed to firstly ensure the validity of earlier studies, as noted above, and, secondly, to preclude the possibility of accidental contamination of larvae or experimental inoculum with viruses from other sources. No instance of DaEPV$_{SR}$ replication was observed.

Experiment A (#05-905261)

The experiment aimed to determine whether consumption of EPV SBs and associated fusolin protein would result in reduced rates of growth of *Helicoverpa armigera* caterpillars. Accordingly, neonate larvae of *H. armigera* were exposed to three dose rates of fusolin in SBs of HaEPV and DaEPV$_{SR}$ (dosages of 5, 50 and 100 μg fusolin/cc diet), and were assessed as described above. Seven days after commencement of the experiment, weights of subsequently "qualifying" larvae (see above) were as shown in Table 3 below:

TABLE 3

Weights of *Helicoverpa armigera* larvae after consumption of diet containing EPV spindle body constituents for seven days.

| treatment | dose (μg/cc diet) | sample size | mean wt (gm) | standard error |
| --- | --- | --- | --- | --- |
| control | none | 23 | 0.0714 | 0.0097 |
| HaEPV | 5 | 27 | 0.0521 | 0.0083 |
| HaEPV | 50 | 21 | 0.0543 | 0.0094 |
| HaEPV | 100 | 16 | 0.0233 | 0.0107 |
| DaEPV$_{SR}$ | 5 | 45 | 0.0642 | 0.0071 |
| DaEPV$_{SR}$ | 50 | 48 | 0.0525 | 0.0069 |
| DaEPV$_{SR}$ | 100 | 44 | 0.0591 | 0.0072 |

Examination of data by analysis of variance (ANOVA) showed no difference between mean weights of larvae in the control group and those fed preparations of DaEPV$_{SR}$ SBs (P=0.2285), but showed that after seven days' exposure, larvae fed HaEPV SBs were significantly smaller than those in the control group (P=0.0201). Analysis of larval response to different dosages of HaEPV SBs failed (P=0.0632) to show evidence of a significant relationship at a 5% confidence level.

These data indicate that short term exposure of *H. armigera* larvae to the constituents of HaEPV SBs can lead to significant reductions in growth of the animal.

Experiment B (#07-90630)

The experiment aimed to determine whether consumption of DaEPV$_{SR}$ SBs would affect growth of *Helicoverpa armigera* larvae if continued for a more lengthy period, or whether consumption for an initial seven day period (as previously tested in Experiment A) would have an observable effect after a longer period of development. Accordingly, neonate larvae of *Helicoverpa armigera* were exposed to three dosages of DaEPV$_{SR}$ fusolin in SBs, and then assessed as described above. After seven days of feeding, larvae were weighed, and for each dosage regime, one sub-group was then allowed to feed on normal diet ("7d expi 7d normal"), while the other continued to feed on a diet containing SBs ("14d exp"). After 7 days, no significant difference was observed between mean weights of control larvae and those exposed to DaEPV$_{SR}$ SBs (P=0.7791); this result is consistent with that reported from Experiment A above. After 14 days, all larvae were reweighed, with results as shown in Table 4 below.

TABLE 4

Weights of *Helicoverpa armigera* larvae after consumption of diet containing EPV spindle body constituents for seven days (with subsequent seven days feeding on regular diet), or continuously for 14 days.

| treatment | fusolin dose (μg/cc diet) | sample size | mean wt (gm) | standard error |
| --- | --- | --- | --- | --- |
| control | none | 9 | 0.4605 | 0.0389 |
| 7 d exp/7 d normal | 5 | 16 | 0.4313 | 0.0348 |
| 14 d exp | 5 | 11 | 0.2194 | 0.0176 |
| 7 d exp/7 d normal | 50 | 17 | 0.4325 | 0.0337 |
| 14 d exp | 50 | 10 | 0.2812 | 0.0185 |
| 7 d exp/7 d normal | 100 | 15 | 0.3850 | 0.0359 |
| 14 d exp | 100 | 9 | 0.2821 | 0.0195 |

Examination of data by analysis of variance (ANOVA) showed no difference between the mean weights of larvae in the control group and those fed preparations of DaEPV$_{SR}$ SBs for 7 days prior to subsequent feeding for a further 7 days on normal diet (P=0.3857). In contrast, highly significant differences were apparent between the mean weights of larvae in the control group and those continuously fed preparations of DaEPV$_{SR}$ SBs for 14 days (P=0.0000), and between mean weights of the "7 day exposure/7 day normal diet" and "14 day continuous exposure" groups (P=0.0000).

This experiment thus indicates that short term exposure of *H. armigera* larvae to the constituents of DaEPV$_{SR}$ SBs has neither short-term nor longer-term consequences, butt that continuous exposure for longer periods (e.g. 14 days) causes highly significant reduction in growth. Taken across all DaEPV$_{SR}$ dosages, mean caterpillar weight was 0.2588 gm after 14 days exposure, as compared to a mean weight of 0.460!5 gm for unexposed animals, representing a reduction in growth of 44%.

Experiment C (#14-91007)

The purpose of this experiment was to determine whether consumption of either HaEPV or DaEPV$_{SR}$ SBs and associated fusolin protein would affect growth of *Spodoptera litura* caterpillars, either after a 7 day period of exposure, a 7 day exposure followed by 5 days' access to normal diet, or continuous exposure for a 12 day period. Accordingly, neonate larvae of *S. litura* were exposed to one dose of SBs and associated fusolin of HaEPV (5 μg fusolin/cc diet), and to two dose rates of DaEPV$_{SR}$ SBs and associated fusolin (5 and 50 μg fusolin/cc diet).

After seven days of feeding larvae were weighed, and for each dosage regime, one sub-group was then allowed to feed on normal diet ("7d exp/5d normal"), while the other continued to feed on diet containing SBs ("12d exp"). After 7 days' feeding activity, no significant differences were observed between mean weights of control larvae and those exposed to various dosages of SBs/fusolin. After a total of 12 days feeding, larvae were reweighed, with results as shown in Table 5 below.

TABLE 5

Weights of *Spodoptera litura* larvae after consumption of diet containing EPV spindle body constituents for seven days (with subsequent five days feeding on regular diet), or continuously for 12 days.

| treatment | fusolin identity and dose (µg/cc diet) | sample size | mean wt (gm) | standard error |
|---|---|---|---|---|
| control | none | 25 | 0.7213 | 0.0464 |
| 7 d exp/5 d normal | HaEPV; 5 | 14 | 0.7174 | 0.0557 |
| 12 d exp | HaEPV; 5 | 11 | 0.1719 | 0.0629 |
| 7 d exp/5 d normal | DaEPV$_{SR}$; 5 | 21 | 0.6829 | 0.0509 |
| 12 d exp | DaEPV$_{SR}$; 5 | 17 | 0.1750 | 0.0566 |
| 7 d exp/5 d normal | DaEPV$_{SR}$; 50 | 16 | 0.5415 | 0.0509 |
| 12 d exp | DaEPV$_{SR}$; 50 | 15 | 0.1520 | 0.0526 |

Examination of data by analysis of variance (ANOVA) showed no difference between the mean weights of larvae in the control group and those fed preparations of either HaEPV or DaEPV$_{SR}$ SBs for 7 days prior to subsequent feeding for a further 5 days on normal diet (P=0.2973). In contrast, highly significant differences were apparent between the mean weights of larvae in the control group and those continuously fed preparations of HaEPV SBs for 12 days (P=0.0000), or DaEPV$_{SR}$ SBs for 12 days (P=0.0000). Likewise, highly significant differences were apparent between the mean weights of larvae in the group fed HaEPV SBs for seven days only before feeding for 5 days on uncontaminated diet, and those continuously fed preparations of HaEPV SBs for 12 days (P=0.0000). Similarly, weights for the same comparison at each dose rate of DaEPV$_{SR}$ SBs were highly significant (P 0.0000 for both dose rates).

These data indicate that short term (i.e., up to 7 days) exposure of *S. litura* larvae to the constituents of HaEPV and DaEPV$_{SR}$ SBs has neither short-term nor longer-term consequences, but that continuous exposure for longer periods (e.g. 12 days) causes highly significant reduction in growth.

EXAMPLE 2

Preparation of Fusolin Negative Recombinant Epv

In this example, the transfer vector pEPAS3 (FIG. 3), which contains a bacterial lacZ gene inserted immediately upstream of the HaEPV fusolin coding sequence, in a manner that prevents expression of the latter, was used, together with wild-type HaEPV, to produce recombinant forms of HaEPV in which fusolin production was replaced by production of the δ-galactosidase marker protein. Amplified stocks of that recombinant HaEPV were subsequently found to contain forms of the virus which produced neither the β-galactosidase marker nor the fusolin protein, as judged by the absence of SBs in preparations viewed by light microscopy. Two such variants (pp5 and pp7) were isolated by repeated plaque purification and subsequent re-amplification in insect cell cultures. Harvested preparations of cells infected with these viruses were then fed to larvae of the moth *Helicoverpa armigera*, establishing, in turn, infections in those insects. Infected insects were processed to recover the products of these infections for use in subsequent biological investigations, and preparations of virus stocks known as pp7T6 and pp7S22 (or, following a second insect passage, pp7T6/5 and pp7S22/13) were ultimately selected for more detailed characterisation.

Stocks of the wild-type clonal isolate wt#2/011293 (Osborne et al., 1996), which was used as the parental form for production of the original β-galactosidase expressing recombinant, were carried in parallel through plaque purification, re-amplification, and feeding to recovery from *H. armigera* insect hosts. Selected lines from these stocks (2C1 and 2D8, or 2C1/11 and 2D8/17) served as controls in the investigations described below.

Light microscopy and scanning electron microscopy was used to examine the composition and morphology of preparations of stocks pp7T6, pp7S22, 2C1 and 2D8. As expected, preparations of the wild-type viruses 2C1 and 2D8 were observed to contain both virus spheroids and SBs, while preparations of the recombinants pp7T6 and pp7S22 were observed to contain only spheroids. The spheroids of all four stocks appeared to be morphologically identical.

The molecular composition of preparations of these virus stocks was examined using the standard laboratory protocols of SDS-PAGE and Western blotting (see, for example, Sambrook et al., 1989). As shown in FIG. 4(*a*), Coomassie Blue staining of the separated protein constituents of all four preparations showed a prominent band of about 115 kDa, corresponding to the major spheroid matrix protein (spheroidin; Hall & Moyer, 1991; Sriskantha et al., 1997), and numerous other less intense bands apparently common to each. Preparations of the two wild-type stocks also showed a band of protein % with a mobility of about 50 kDa, (FIG. 4[*a*], arrow) corresponding to the monomeric form of the fusolin protein (Dall et Cd., 1993), that was not apparent in preparations of pp7T6 and pp7S22. A polyclonal antiserum to HaEPV fusolin protein (Dall et al., 1993) and Western blotting protocols were then used to further characterise these virus stocks. As shown in FIG. 4(*b*), both preparations of wild-type virus produced very prominent immuno-reactive bands at a position corresponding to a molecular weight of about 50kDa (arrow), which, as expected, were not apparent in preparations of the two fusolin negative [fus$^{(-)}$] recombinant forms.

Feeding studies With Fusolin Negative Recombinant EPV

One wild-type isolate (2D8) and one recombinant (pp7T6) were then selected for more detailed biological characterisation. Individually housed 48 hour old *H. armigera* larvae were exposed to a range of quantities of each of the viruses by placing them on artificial diet spread with aliquots of virus dilution series. Seven days later ("post-infection"; 7 dpi) each larvae was weighed and at 21 dpi all larvae were collected, their developmental stage was recorded, and their status with respect to viral infection (i.e. infected or uninfected) was determined by examination of fat body smears by light microscopy. In all instances, larvae that died at or before 7 dpi were excluded from the assay, while those that were dead at 21 dpi were considered to be positive (i.e. infected).

As shown in FIG. 5, these experiments demonstrated that the wild-type virus isolate 2D8 was substantially more infectious than the fus$^{(-)}$ recombinant pp7T6, with the former having an estimated IC$_{50}$ (this being the quantity of virus required to infect 50% of exposed larvae) of 0.2 spheroids/mm² diet (sph/mm²), while for pp7T6 it was 35 sph/mm². Results of less detailed investigations with virus isolates 2C1 and pp7S22 were also consistent with these results.

Further analysis of the results has revealed, in addition, another fusolin associated phenomenon which has not previously been recognised, namely, that the presence of fusolin is associated with retardation of the rates of growth and development of exposed insect larvae. Thus, FIG. 6 shows mean weights of infected insects only, taken at 7 dpi, and calculated as a proportion of the weight of uninfected larvae from the same cohort (i.e. as a % of the weight of experimental controls). As can be observed, when the results were analysed in this manner it was clear that in the presence of fusolin, larval weight gain was much reduced. This analysis thus makes allowance for the previously described observation (i.e. that the presence of fusolin enhances virus infectivity), and further shows that when intrinsic infectivity of a particular dose is used as the basis of comparison, this previously unrecognised effect of fusolin on insect growth can be observed.

Similarly, and as shown in FIG. 7, when the developmental fate of those same infected insects, now pooled in three "categories" of infection rates, was assessed at 21 dpi, a much reduced proportion of larvae was observed to proceed to pupation in samples exposed to preparations of the wild type virus containing the fusolin protein.

The above examples demonstrate the feasibility of strategies designed to effect oral ingestion of constituent SB/SLB protein(s) such as fusolin by feeding insects as a means of inhibiting feeding, growth and/or development of such insects. Such strategies may therefore be of significant value with respect to limiting losses to commodity materials that result from insect feeding activity. That is, it can be appreciated that small insects cause less feeding damage to plants than do larger ones, and that retarding the growth and/or development of insects will increase the time-span during which factors such as adverse environmental conditions, predators, and/or artificially applied chemical and biological agents may effect their control. In addition, it is widely recognised that early instar (i.e., smaller) insects are intrinsically more susceptible to infection with, or the activity of, a variety of chemical and biological control agents such as the bacterium *Bacillus thuringiensis* ("Bt").

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

Adams J R., McClintock J T. Baculoviridae. Nuclear polyhedrosis viruses. Part 1. Nuclear polyhedrosis viruses of insects. In J R Adams, J. R. Bonami, editors: Atlas of Invertebrate Viruses, Boca Raton: CRC Press, 1991. p 87–204.

Adams J R, Wilcox T A., Histopathology of the almond moth, *Cadra cautella*, infected with a nuclear-polyhedrosis virus. J Inverter Pathol 1968;12:269–274.

Ahrens C H, Russell R L, Funk C J, Evans J T, Harwood S H, Rohrmann G F. The sequence of the Orgyia pseudotsugata multinucleocapsid nuclear polyhedrosis virus genome. Virology 1997;229: 381–399.

Altschul S F, Gish W, Miller W, Myers E W, Lipman D J. Basic local alignment search tool. J. Mol. Biol. 1990;215: 403–410.

Arif B M. Recent advances in the molecular biology of entomopoxviruses. J Gen Virol 1995;76:1–13.

Ayres M D, Howard S C, Kuzio J, Lopez-Ferber M, Possee R D. The complete DNA sequence of *Autographa californica* nuclear polyhedrosis virus. Virology 1994;202: 586–605.

Cunningham J C. An ultrastructural study of the development of a nuclear polyhedrosis virus of the eastern hemlock looper, *Lambdina fiscellaria fiscellaria*. Can J Microbiol 1971;17:69–72.

Dall D J, Sriskantha A, Vera A P, Lai-Fook J, Symonds T M. A gene encoding a highly expressed spindle body protein of *Heliothis armigera* entomopoxvirus. J Gen Virol 1993; 74:1811–1818.

Devereux J. Heaberli P, Smithies O. A comprehensive set of sequence analysis programs for the VAX. Nuc Acids Res 1984;12:387–395.

Fernon C A, Vera A P, Crnov R, Lai-Fook J, Osborne R J, Dall D J. In vitro replication of *Heliothis armigera* EPV. J Invertebr Pathol 1995;66:216–223.

Gomi S, Majima K, Maeda S. Sequence analysis of the genome of *Bombyx mori* nucleopolyhedrovirus. J Gen Virol 1999;80:1323–1337.

Goodwin R H, Milner R J, Beaton C D. Entomopoxvirinae. In J R Adams, J. R. Bonami, editors: Atlas of Invertebrate Viruses, Boca Raton: CRC Press, 1991. p 393–434.

Gross C H, Wolgamot G M, Russell R L Q, Pearson M N, Rohrmann G F. A 37-kilodalton glycoprotein from a baculovirus of *Orgyia pseudotsugata* is localized to cytoplasmic inclusion bodies. J Virol 1993;67:469–475.

Hall R L, Moyer R W. Identification, cloning, and sequencing of a fragment of *Amsacta moorei* entomopoxvirus DNA containing the spheroidin gene and three vaccinia virus-related open reading frames. J Virol 1991;65:6516–6527.

Hayakawa T, Xu J, Hukahara, T. Cloning and sequencing of the gene for an enhancing factor from *Pseudaletia separata* entomopoxvirus. Gene 1996;177:269–270.

Hayakawa T, Ko R, Okano K, Seong SI, Goto C, Maeda S. Sequence analysis of the *Xestia c-nigrum* granulovirus genome. Virology 1999;262:277–297.

Huger A M, Krieg A. On spindle-shaped cytoplasmic inclusions associated with a nuclear polyhedrosis of *Choristoneura murinana*. J Invertebr Pathol 1968;12:461–462.

Hukuhara T, Hayakawa T, Wijonarko A. Increased baculovirus susceptibility of armyworm larvae feeding on transgenic rice plants expressing an entomopoxvirus gene. Nature Biotechnology 1999;17:1122–1124.

Kuzio J, Pearson M N, Harwood S H, Funk C J, Evans J T, Slavicek J M, Rohrmann G F. Sequence and analysis of the genome of a baculovirus pathogenic for *Lymantria dispar*. Virology 1999;253:17–34.

Lai-Fook J, Dall D J. Spindle bodies of *Heliothis armigera* entomopoxvirus develop in structures associated with host cell endoplasmic reticulum. J Invertebr Pathol (in press).

Liu J J, Carstens E B. Identification, molecular cloning, and transcription analysis of the *Choristoneura fumiferana* nuclear polyhedrosis virus spindle-like protein gene. Virology 1996;223: 396–400.

Mitsuhashi W, Furuta Y, Sato M. The spindles of an entomopoxvirus of

Coleoptera (*Anomala cuprea*) strongly enhance the infectivity of a nucleopolyhedrovirus in *Lepidoptera*(*Bombyx mori*). J. Invertebr. Pathol. 1998;71:186–188.

Moss, B. Poxyiridae: the viruses and their replication. In B N Fields, D M Knipe and P M Howley, editors: Fields Virology. Philadelphia, Lippincott-Raven Publishers, 1996. p 2637–2671.

Murphy, F. A., Fauquet, C. M., Bishop, D. H. L., Ghabrial, S. A., Jarvis, A. W., Martelli, G. P., Mayo, M. A., and Summers, M. D. (editors) Virus Taxonomy. Sixth Report of the International Committee on Taxonomy of Viruses. Vienna & New York: Springer-Verlag, 1995.

Osborne R J, Symonds T M, Sriskantha A, Lai-Fook J, Fernon C A, Dall D J. An entomopoxvirus homologue of the vaccinia virus D13L-encoded "rifampicin resistance" protein. J Gen Virol 1996;77:839–846.

Phanis C G, Miller D P, Cassar S C, Tristem M, Thiem S M, O'Reilly D R. Identification and expression of two baculovirus gp37 genes. J Gen Virol 1999;80:1823–1831.

Sambrook J, Fritscli E F, Maniatis T. Molecular Cloning: A Laboratory Manual, 2nd edn. New York: Cold Spring Harbor Laboratory.

Smirnoff W A. Rhombohedral twisted crystalloids found in the cytoplasm of nuclear polyhedrosis infected larvae of the ugly-nest caterpillar. Can J Microbiol 1970;1¢:906–907.

Sriskantha A, Osborne R J, Dall D J. Mapping of the *Heliothis armigera* entomopoxvirus (HaEPV) genome, and analysis of genes encoding the HaEPV spheroidin and nucleoside triphosphate phosphohydrolase I proteins. J Gen Virol 1997;78:3115–3123.

Xu J, Hukuhara T. Enhanced infection of a nuclear polyhedrosis virus in larvae of the armyworm, *Pseudaletia separata*, by a factor in the spheroids of an entomopoxvirus. J Invertebr Pathol 1992;60:259–264.

Xu J, Hukuhara T. Biochemical properties of an enhancing factor of an entomopoxvirus. J Invertebr Pathol 1994;63: 14–18.

---

What is claimed is:

1. A plant transformed with at least one polynucleotide molecule comprising a nucleotide sequence encoding an insect virus fusolin protein or a fusolin-like protein, said nucleotide sequence being operably linked to a suitable promoter sequence, wherein said transformed plant expresses said fusolin protein or fusolin-like protein in plant tissue or tissues susceptible to damage by feeding insects.

2. A plant according to claim 1, wherein the fusolin protein is selected from fusolins from *Heliothis armigera* (HaEPV), *Pseudaletia separate* EPV (PsEPV), *Chorisioneura biennis* EPV (CbEPV) and *Dermolepida albohirtum* EPV.

3. A plant according to claim 1, wherein the fusolin-like protein is selected from fusolin-like proteins from *Autographa californica* (AcMNPV), *Bombyx mori* (BmMNPV), *Choristoneura fumiferana* (CfMNPV), *Lymantria dispar* (LdMNPV), *Orgyia pseudotsugata* NPVs (OpMNPV) and *Xestia c-nigrim* GV (XcGV).

4. A plant according to claim 1 which further expresses an exogenous toxin or other agent that is deleterious to insects.

5. A plant according to claim 4, wherein the exogenous toxin is selected from *Bacillus thuringiensis* δ-toxin and insect neurohormones.

6. A method of controlling or preventing damage caused to a plant according to claim 1 from feeding insects, said method comprising applying to said plant an insecticidal chemical and/or insecticidal biological agent.

7. A method according to claim 6, wherein the insecticidal chemical is selected from organophosphate compounds.

8. A method according to claim 6, wherein the biological agent is selected from bacteria pathogenic to insects.

9. A method according to claim 6, wherein the biological agent is selected from insect viruses.

10. A method for inhibiting growth or development of an insect, the method comprising cultivating a plant according to claim 1 where it can be accessed by insect larvae, wherein upon ingestion of the plant, growth or development of the insect is inhibited.

* * * * *

SEQUENCE LISTING

```
<160> NUMBER OF SEQ ID NOS: 18

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: conserved
      sequence of fusolin proteins

<400> SEQUENCE: 1

Val Arg Trp Gln Arg
1               5

<210> SEQ ID NO 2
<211> LENGTH: 13
<212> TYPE: PRT
<213> ORGANISM: Dermolepida albohirtum entomopoxvirus and Melolontha
      melolotha entomopoxvirus

<400> SEQUENCE: 2

His Gly Tyr Ile Thr Phe Pro Ile Ala Arg Gln Arg Arg
1               5                   10

<210> SEQ ID NO 3
<211> LENGTH: 13
<212> TYPE: PRT
<213> ORGANISM: Anomala cuprea entomopoxvirus

<400> SEQUENCE: 3

His Gly Tyr Val Thr Phe Pro Ile Ala Arg Gln Arg Arg
1               5                   10

<210> SEQ ID NO 4
<211> LENGTH: 13
<212> TYPE: PRT
<213> ORGANISM: Choristoneura biennis entomopoxvirus, Helicoverpa
      armigera entomopoxvirus and Pseudaletia separata entomopoxvirus

<400> SEQUENCE: 4

His Gly Tyr Met Thr Phe Pro Ile Ala Arg Gln Arg Arg
1               5                   10
```

```
<210> SEQ ID NO 5
<211> LENGTH: 13
<212> TYPE: PRT
<213> ORGANISM: Bombyx mori nuclear polyhedrosis virus

<400> SEQUENCE: 5

His Gly Tyr Leu Ser Leu Pro Thr Ala Arg Gln Tyr Lys
1               5                   10

<210> SEQ ID NO 6
<211> LENGTH: 13
<212> TYPE: PRT
<213> ORGANISM: Choristoneural fumiferana nuclear polyhedrosis virus

<400> SEQUENCE: 6

His Gly Tyr Leu Ser Val Pro Val Ala Arg Gln Tyr Lys
1               5                   10

<210> SEQ ID NO 7
<211> LENGTH: 13
<212> TYPE: PRT
<213> ORGANISM: Mamestra brassica nuclear polyhedrosis virus

<400> SEQUENCE: 7

His Gly Tyr Leu Ser Tyr Pro Val Ala Arg Gln Tyr Lys
1               5                   10

<210> SEQ ID NO 8
<211> LENGTH: 13
<212> TYPE: PRT
<213> ORGANISM: Xestria c-nigrum GV

<400> SEQUENCE: 8

His Gly Phe Met Leu Tyr Pro Leu Ala Arg Gln Tyr Arg
1               5                   10

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Seqeunce: PCR primer
<220> FEATURE:
<221> NAME/KEY: misc_feature
<222> LOCATION: (3)..(3)
<223> OTHER INFORMATION: y = c or t
<220> FEATURE:
<221> NAME/KEY: misc_feature
<222> LOCATION: (6)..(6)
<223> OTHER INFORMATION: w = a or t
<220> FEATURE:
<221> NAME/KEY: misc_feature
<222> LOCATION: (12)..(12)
<223> OTHER INFORMATION: r= a or g
<220> FEATURE:
<221> NAME/KEY: misc_feature
<222> LOCATION: (15)..(15)
<223> OTHER INFORMATION: n = a, t, c or g

<400> SEQUENCE: 9
cayggwtata trcantttcc tatagc                                          26

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: PCR Primer
<220> FEATURE:
```

```
<221> NAME/KEY: misc_feature
<222> LOCATION: (4)..(4)
<223> OTHER INFORMATION: r = a or g
<220> FEATURE:
<221> NAME/KEY: misc_feature
<222> LOCATION: (7)..(7)
<223> OTHER INFORMATION: r = a or g
<220> FEATURE:
<221> NAME/KEY: misc_feature
<222> LOCATION: (10)..(10)
<223> OTHER INFORMATION: r = a or g
<220> FEATURE:
<221> NAME/KEY: misc_feature
<222> LOCATION: (13)..(13)
<223> OTHER INFORMATION: w = a or t
<220> FEATURE:
<221> NAME/KEY: misc_feature
<222> LOCATION: (19)..(19)
<223> OTHER INFORMATION: w = a or t
<220> FEATURE:
<221> NAME/KEY: misc_feature
<222> LOCATION: (22)..(22)
<223> OTHER INFORMATION: y = c or t

<400> SEQUENCE: 10
acarttrtar aawccttcwc cyac                                              24

<210> SEQ ID NO 11
<211> LENGTH: 220
<212> TYPE: PRT
<213> ORGANISM: Dermolepida albohirtum entomopoxvirus

<400> SEQUENCE: 11

His Gly Tyr Ile Thr Phe Pro Ile Ala Arg Gln Arg Arg Cys Asn Val
  1               5                  10                  15

Gln Gly Gly Phe Trp Trp Pro Thr Asp Gly Ser Ala Ile Pro Asp Pro
             20                  25                  30

Met Cys Arg Ala Ala Tyr Gln Asn Val Phe Asn Thr Val Leu Gln Gln
         35                  40                  45

Gly Gly Ser Leu Asn Gln Ala Ala Thr Ala Ala Gln Tyr Met Phe Gln
     50                  55                  60

Gln Asp Asn Glu Tyr Ala Ala Leu Ala Gly Ser Asn Phe Arg Asp Leu
 65                  70                  75                  80

Asn His Ile Gln Asn Asn Val Val Pro Phe Asp Leu Cys Ala Ala Gly
                 85                  90                  95

Ala Asn Asn Trp Arg Arg Val Pro Phe Gly Asp Lys Ser Gly Met Asp
            100                 105                 110

Ile Ser Gly Ser Trp Thr Pro Thr Gly Ile Pro Leu Glu Ser Asn Thr
        115                 120                 125

Val Gly Thr Gly Pro Ile Glu Phe Glu Phe Cys Pro Thr Ala Ile His
    130                 135                 140

Glu Pro Ser Phe Phe Glu Ile Tyr Ile Thr Val Pro Asn Phe Asn Val
145                 150                 155                 160

Phe Thr Asp Gln Val Thr Trp Ser Gln Leu Glu Asn Ile Phe Thr Gly
                165                 170                 175

Pro Ile Pro Leu Val Ala Arg Arg Pro Asp Ser Leu Cys Asn Ala Asn
            180                 185                 190

Ser Arg Val Tyr Arg Ile Thr Val Gly Ile Pro Met Arg Gln Thr Gln
        195                 200                 205

Phe Val Leu Tyr Val Arg Trp Gln Arg Ile Asp Pro
    210                 215                 220
```

<210> SEQ ID NO 12
<211> LENGTH: 220
<212> TYPE: PRT
<213> ORGANISM: Melolontha melolotha entomopoxvirus

<400> SEQUENCE: 12

```
His Gly Tyr Ile Thr Phe Pro Ile Ala Arg Gln Arg Cys Asn Val
1               5                   10                  15

Gln Gly Gly Phe Trp Trp Pro Gly Gly Ser Gly Ile Pro Asp Pro
            20                  25                  30

Met Cys Arg Ala Ala Tyr Gln Asn Val Tyr Asn Lys Val Leu Gln Gln
            35                  40                  45

Gly Gly Thr Ile Asp Gln Ala Ala Ser Ala Ala Gln Tyr Met Phe Gln
        50                  55                  60

Gln Asp Asn Glu Tyr Ala Ala Leu Ala Gly Pro Asn Tyr Leu Asp Gln
65                  70                  75                  80

Asn His Ile Arg Asn Asn Val Val Pro Asn Tyr Leu Cys Ala Ala His
                85                  90                  95

Ala Thr Thr Trp Arg Ile Arg Pro Phe Gly Asp Lys Thr Gly Met Asp
            100                 105                 110

Val Ser Gly Ser Trp Thr Pro Thr Val Ile Pro Leu Gln Asp Asn Thr
        115                 120                 125

Val Ser Thr Val Pro Ile Glu Phe Glu Phe Cys Pro Thr Ala Ile His
    130                 135                 140

Glu Pro Ser Phe Phe Glu Ile Tyr Ile Thr Val Pro Ser Phe Asn Val
145                 150                 155                 160

Tyr Thr Asp Gln Val Thr Trp Gln Gln Leu Ile Asn Ile Phe Thr Gly
                165                 170                 175

Pro Ile Pro Leu Val Gln Arg Arg Pro Asp Ser Gln Cys Asn Ala His
            180                 185                 190

Asn Leu Val Tyr Arg Thr Thr Val Gly Ile Pro Val Arg Gln Thr Gln
        195                 200                 205

Phe Val Leu Tyr Val Arg Trp Gln Arg Asn Asp Pro
    210                 215                 220
```

<210> SEQ ID NO 13
<211> LENGTH: 220
<212> TYPE: PRT
<213> ORGANISM: Anomala cuprea entomopoxvirus

<400> SEQUENCE: 13

```
His Gly Tyr Val Thr Phe Pro Ile Ala Arg Gln Arg Cys Asn Val
1               5                   10                  15

Gln Gly Gly Phe Trp Trp Pro Glu Gly Thr Asn Ile Pro Asp Pro
            20                  25                  30

Met Cys Arg Ala Ala Tyr Gln Tyr Val Phe Asn Lys Val Leu Ser Glu
            35                  40                  45

Gly Gly Ser Thr Ser Gln Ala Ala Ser Ala Ala Gln Tyr Met Phe Gln
        50                  55                  60

Gln Asp Asn Glu Tyr Ala Ala Leu Ala Gly Pro Asn Phe Arg Asp Ile
65                  70                  75                  80

Cys Trp Ile Lys Glu Gln Val Val Pro Asp Tyr Leu Cys Ala Ala Gly
                85                  90                  95

Ala Asp Thr Trp Arg Ile Arg Pro Phe Gly Asp Lys Thr Gly Met Asp
            100                 105                 110

Ile Val Gly Ser Trp Pro Pro Thr Val Ile Pro Leu Glu Asn Asn Phe
```

-continued

```
                115                 120                 125
Val Asn Thr Ile Pro Ile Glu Leu Glu Phe Cys Pro Thr Ala Ile His
    130                 135                 140

Glu Pro Ser Tyr Phe Glu Val Tyr Val Thr Thr Pro Glu Phe Asn Val
145                 150                 155                 160

Tyr Arg Asp Lys Val Thr Trp Pro Leu Leu Glu Leu Val Phe Asn Ser
                165                 170                 175

Thr Val Pro Leu Val Asn Arg Arg Ala Asp Ser Leu Cys Thr Ala Asn
            180                 185                 190

Ala Arg Val Tyr Arg Met Ile Val Pro Val Pro Tyr Arg Gln Thr Gln
        195                 200                 205

Phe Val Ile Tyr Val Arg Trp Gln Arg Ile Asp Pro
    210                 215                 220

<210> SEQ ID NO 14
<211> LENGTH: 221
<212> TYPE: PRT
<213> ORGANISM: Choristoneura biennis entomopoxvirus

<400> SEQUENCE: 14

His Gly Tyr Met Thr Phe Pro Ile Ala Arg Gln Arg Cys Ser Ala
1               5                   10                  15

Ala Gly Gly Asn Trp Tyr Pro Val Gly Gly Gly Ile Gln Asp Pro
            20                  25                  30

Met Cys Arg Ala Ala Tyr Gln Asn Val Phe Asn Lys Val Leu Asn Ser
        35                  40                  45

Asn Gly Gly Asp Val Ile Asp Ala Ser Glu Ala Ala Asn Tyr Met Tyr
    50                  55                  60

Thr Gln Asp Asn Glu Tyr Ala Ala Leu Ala Gly Pro Asp Tyr Thr Asn
65                  70                  75                  80

Ile Cys His Ile Gln Gln Arg Val Val Pro Ser Tyr Leu Cys Ala Ala
                85                  90                  95

Gly Ala Ser Asp Trp Ser Ile Arg Pro Phe Gly Asp Lys Ser Gly Met
            100                 105                 110

Asp Leu Pro Gly Ser Trp Thr Pro Thr Ile Ile Gln Leu Ser Asp Asn
        115                 120                 125

Gln Gln Ser Asn Val Val Met Glu Leu Glu Phe Cys Pro Thr Ala Val
    130                 135                 140

His Asp Pro Ser Tyr Tyr Glu Val Tyr Ile Thr Asn Pro Ser Phe Asn
145                 150                 155                 160

Val Tyr Thr Asp Asn Val Val Trp Ala Asn Leu Asp Leu Ile Tyr Asn
                165                 170                 175

Asn Thr Val Thr Leu Arg Pro Lys Leu Pro Glu Ser Thr Cys Ala Ala
            180                 185                 190

Asn Ser Met Val Tyr Arg Phe Glu Val Ser Ile Pro Val Arg Pro Ser
        195                 200                 205

Gln Phe Val Leu Tyr Val Arg Trp Gln Arg Ile Asp Pro
    210                 215                 220

<210> SEQ ID NO 15
<211> LENGTH: 220
<212> TYPE: PRT
<213> ORGANISM: Helicoverpa armigera entomopoxvirus

<400> SEQUENCE: 15

His Gly Tyr Met Thr Phe Pro Ile Ala Arg Gln Arg Cys Ser Val
```

-continued

```
1               5                   10                  15

Arg Gly Gly Gln Trp Trp Pro Pro Asn Gly Asp Gly Ile Thr Asp Thr
            20                  25                  30

Met Cys Arg Ala Ala Tyr Gln Asn Val Tyr Asn Lys Val Leu Asn Gln
        35                  40                  45

Tyr Asn Asp Pro Gln Glu Ala Ala Thr Ala Ala Gln Tyr Met Phe Gln
    50                  55                  60

Gln Asp Asn Glu Tyr Ala Ala Leu Ala Gly Pro Asp Tyr Thr Asn Leu
65                  70                  75                  80

Cys Asn Leu Gln Gln Asn Val Val Pro Asn Asn Leu Cys Ala Ala Gly
                85                  90                  95
Ala Asp Asp Trp Asp Val Val Pro Phe Gly Asp Lys Ser Gly Met Asp
            100                 105                 110
Leu Pro Gly Asn Trp Val Pro Thr Val Ile Pro Leu Asp Ser Asn His
        115                 120                 125
Gln Ser Ser Val Ala Leu Glu Leu Glu Phe Cys Pro Thr Ala Val His
    130                 135                 140
Asp Pro Ser Tyr Tyr Glu Val Tyr Ile Thr Asn Ser Gly Phe Asn Val
145                 150                 155                 160
His Thr Asp Asn Val Val Trp Gly Asn Leu Glu Leu Ile Phe Asn Asp
                165                 170                 175
Thr Val Pro Leu Arg Pro Lys Ser Ser Thr Ser Thr Cys Asn Ala Asn
            180                 185                 190
Pro Asn Val Tyr Arg Phe Thr Val Ser Ile Pro Val Arg Pro Ala Gln
        195                 200                 205
Phe Val Leu Tyr Val Arg Trp Gln Arg Ile Asp Pro
    210                 215                 220

<210> SEQ ID NO 16
<211> LENGTH: 217
<212> TYPE: PRT
<213> ORGANISM: Bombyx mori nuclear polyhedrosis virus

<400> SEQUENCE: 16

His Gly Tyr Leu Ser Leu Pro Thr Ala Arg Gln Tyr Lys Cys Phe Lys
1               5                   10                  15

Gly Gly Asn Phe Tyr Trp Pro His Asn Gly Asp Lys Ile Pro Asp Ala
            20                  25                  30

Ala Cys Arg Asn Ala Tyr Lys Ser Val Tyr Tyr Lys Tyr Arg Ala Leu
        35                  40                  45

Asp Leu Glu Ser Gly Ala Ala Ala Ala Thr Ala Gln Tyr Met Phe Gln
    50                  55                  60

Gln Tyr Met Glu Tyr Ala Ser Val Ala Gly Pro Asn Tyr Asp Asp Phe
65                  70                  75                  80

Asp Leu Ile Lys Gln Arg Val Val Pro His Thr Leu Cys Gly Ala Gly
                85                  90                  95

Ser Asn Asp Arg Asn Ser Val Phe Gly Asp Lys Ser Gly Met Asp Glu
            100                 105                 110

Pro Phe Asn Asn Trp Lys Pro Asn Thr Leu Tyr Leu Asn Leu Tyr Gln
        115                 120                 125

Pro Val Tyr Arg Met Asn Val His Phe Cys Pro Thr Ala Ile His Glu
    130                 135                 140

Pro Ser Tyr Phe Glu Val Phe Ile Thr Lys Ser Asn Trp Asp Arg Arg
145                 150                 155                 160
```

```
Asn Pro Ile Thr Trp Asn Glu Leu Glu Tyr Ile Gly Gly Asn Asp Ser
            165                 170                 175

Asp Leu Ile Pro Asn Pro Gly Asp Pro Leu Cys Asp Asn Ser Leu Val
            180                 185                 190

Tyr Ser Ile Pro Val Val Ile Pro Tyr Arg Ser Asn Gln Phe Val Met
            195                 200                 205

Tyr Val Arg Trp Gln Arg Ile Asp Pro
        210                 215

<210> SEQ ID NO 17
<211> LENGTH: 217
<212> TYPE: PRT
<213> ORGANISM: Choristoneural fumiferana nuclear polyhedrosis virus

<400> SEQUENCE: 17

His Gly Tyr Leu Ser Val Pro Val Ala Arg Gln Tyr Lys Cys Phe Arg
1               5                   10                  15

Asp Gly Asn Phe Trp Trp Pro Asn Gly Asp Asn Ile Pro Asp Glu
            20                  25                  30

Ala Cys Arg Asn Ala Tyr Lys Lys Val Tyr Tyr Lys Tyr Arg Ala Ile
            35                  40                  45

Asn Val Pro Ser Gln Glu Ala Ala Ser Ala Ala Gln Tyr Met Phe Gln
        50                  55                  60

Gln Tyr Thr Glu Tyr Ala Ala Leu Ala Gly Pro Asn Tyr Leu Asp Phe
65                  70                  75                  80

Asp Met Val Lys Arg Asp Val Val Pro His Thr Leu Cys Gly Ala Ala
                85                  90                  95

Ser Asn Asp Arg Ala Ala Leu Phe Gly Asp Lys Ser Gly Met Asp Glu
            100                 105                 110

Pro Phe Tyr Asn Trp Arg Pro Asp Val Leu Tyr Met Asn Arg Tyr Gln
        115                 120                 125

Asn Ser Tyr Pro Met Asp Val His Phe Cys Pro Thr Ala Ile His Glu
    130                 135                 140

Pro Ser Tyr Phe Glu Val Phe Val Thr Lys Ser Thr Trp Asp Arg Arg
145                 150                 155                 160

Asn Pro Ile Thr Trp Asn Glu Leu Glu Tyr Ile Gly Gly Asn Asn Ser
            165                 170                 175

Gly Leu Val Pro Asn Pro Gly Asp Pro Leu Cys Asp Ser Asn Gln Ile
            180                 185                 190

Tyr Ser Ile Pro Val Ser Val Pro Tyr Arg Ser Gly Gln Phe Val Met
            195                 200                 205

Tyr Val Arg Trp Gln Arg Ile Asp Pro
        210                 215

<210> SEQ ID NO 18
<211> LENGTH: 207
<212> TYPE: PRT
<213> ORGANISM: Xestria c-nigrum GV

<400> SEQUENCE: 18

His Gly Phe Met Leu Tyr Pro Leu Ala Arg Gln Tyr Arg Cys Tyr Ala
1               5                   10                  15

Pro Gln Asp Phe Tyr Trp Pro Asp Asp Gly Ser Asn Ile Gln Asn Pro
            20                  25                  30

Ala Cys Lys Leu Ala Phe Gln His Val Tyr Arg Asn Ser Gly Ser Ala
            35                  40                  45
```

```
Ala Ala Gln Tyr Met Phe Val Gln Tyr Ala Glu Tyr Ala Ala Leu Ala
    50              55                  60
Gly Ser Asn Tyr Asn Asp Met Gln His Ile Gln Gln Asp Val Val Pro
65              70                  75                      80
Asn Phe Leu Cys Ser Ala Ala Ala Asp Asn Thr Ser Thr Pro Tyr Gly
                85                  90                  95
Asp Lys Ser Gly Ile Ser Leu Pro Ser Asp His Trp Gln Thr Thr Ile
                100             105                 110
Ile Asn Asp Arg Gly His Thr Gln Leu Tyr Tyr Cys Pro Thr Val Pro
        115                 120             125
His Asp Pro Ser Phe Phe Gln Val Phe Val Thr Lys Lys Asp Phe Asp
    130                 135                 140
Val Gly Thr Thr Ile Val Thr Trp Asn Asp Leu Glu Leu Val His Glu
145             150                 155                     160
Gln Ser Ala Val Ile Val Pro Asn Ser Arg Thr Val Pro Asn Ser Glu
                165             170                 175
Glu Cys Gly Ala Phe Val Tyr Ser Ile Asp Ala Thr Leu Pro Met Arg
            180             185             190
Ser Lys Pro Phe Val Val Phe Val Arg Trp Gln Arg Glu Asp Pro
        195             200             205
```